(12) United States Patent
Karapetyan

(10) Patent No.: US 6,948,505 B2
(45) Date of Patent: Sep. 27, 2005

(54) CLEANING APPARATUS FOR MEDICAL AND/OR DENTAL TOOL

(76) Inventor: Armen Karapetyan, 1935 N. Van Ness Ave., Los Angeles, CA (US) 90068

( * ) Notice: Subject to any disclaimer, the term of this patent is extended or adjusted under 35 U.S.C. 154(b) by 321 days.

(21) Appl. No.: 10/361,429

(22) Filed: Feb. 10, 2003

(65) Prior Publication Data

US 2004/0154652 A1 Aug. 12, 2004

(51) Int. Cl.[7] .............................................. B08B 3/04
(52) U.S. Cl. .................. 134/166 R; 134/170; 134/182; 422/292; 422/300
(58) Field of Search .......................... 422/26, 305, 292, 422/298, 300, 1, 297; 137/1; 134/104.2, 166 R, 169 R, 170, 166 C, 182, 184, 200, 102.1, 3, 111, 148, 151, 22.1, 22.11, 22.18, 167 C; 222/1, 207, 494

(56) References Cited

U.S. PATENT DOCUMENTS

| | | | |
|---|---|---|---|
| 2,243,093 A | * | 5/1941 | Flahive ........................ 202/170 |
| 4,892,112 A | | 1/1990 | Knetsch |
| 5,415,248 A | | 5/1995 | Eibl et al. |
| 5,505,218 A | | 4/1996 | Stainhauser |
| 5,961,937 A | * | 10/1999 | Gobbato ....................... 422/300 |
| 6,263,887 B1 | * | 7/2001 | Dunn ........................ 134/22.18 |

* cited by examiner

*Primary Examiner*—Michael Barr
*Assistant Examiner*—Sarah E. Husband

(57) ABSTRACT

A cleaning apparatus for medical and/or dental tool provides a possibility to clean the burrs and brushes (files) of the remained tooth material on them after operation on patient. An improved cleaning apparatus for medical and/or dental tool includes a container, comprising a neck with an opening and at least one of a plurality of apertures located in the lower part of the neck, a fluid stream reflector of a lid, which includes a connector comprising a fluid inlet pipe which is coupled by a tubular means with a fluid line via controllable valve, and a cylindrical stand connected to the base, providing a stable position of the container during cleaning process.

5 Claims, 4 Drawing Sheets

CLEANING APPARATUS FOR MEDICAL AND/OR DENTAL TOOL

FIELD OF THE INVENTION

This invention is generally related to an apparatus intended for medical and/or dental tool cleaning and more particularly for cleaning treatment of the dental burrs and files (brushes) used in the drilling and handpiece tool.

BACKGROUND OF THE INVENTION

The dental tools, such as the burrs and brushes (files) of high speed and/or low speed dental drill or handpieces, are in wide use, and a dentist will commonly use the same dental tool especially the burrs and brushes for performing several dental operations on different patients in a short period of time. There is a need for a convenient, economical and effective apparatus/devices to help the dentist and his or her staff to clean (and later to sanitize) the tools between operations on patients. Furthermore, a routine is needed that would help to insure that all portions of a burrs and files, which have been exposed to one patient's mouth, are cleaned of the remained tooth material on the tool prior to sanitize and use with other patients. Such additional procedure would provide one more safeguard against the spread of disease.

The various types of the devices for cleaning of the dental removable tool are well known.

For example, the apparatus by U.S. Pat. No. 5,415,248 provides the cleaning and/or lubrication of the medical/dental tool. This apparatus for cleaning dental tools includes an instrument connection for blowing oil and/or cleaning agent, possibly in the form of a spray mist, through the instruments and subsequently drying the instruments with compressed air. The control of the various cleaning phases and of the conveyance of the cleaning liquids takes place pneumatically. In particular, a short-term flow of compressed air displaces at least one piston against a spring which causes oil and/or cleaning agent to be pressed into the instrument. A control edge of the piston produces a connection between the compressed air supply and the instrument connection when the piston leaves its upper position of rest. When the piston travels back in the opposite direction under the force of the spring after the short-term flow of compressed air has ended, the supply of oil and/or cleaning agent to the instrument connection is interrupted, while the supply of compressed air is maintained until the piston has again reached its upper position of rest. In the mentioned apparatus an external compressed air is supplied to the apparatus and reaches a tee in which a pressure reduction and/or a purification by means of an inserted filter may be carried out. The compressed air reaches from the tee through a line to an actuating button which starts the cleaning procedure when being pressed down. When the button is pressed downwardly against the force of a spring, the supply of compressed air and the continuing line are connected to each other for a relatively short time, so that compressed air is conducted from the tee through the actuating button to the head of a regulating unit. A piston is provided in the interior of the regulating unit. A spring presses the piston upwardly against the head of the regulating unit. When compressed air is admitted to the regulating unit, the piston is pressed downwardly against the force of the spring, and the piston rod, constructed as a double piston, presses oil into the line and cleaning agent into the line. A return flow of the two fluids into the lines is prevented by check valves in the cleaning agent line and by two analogous check valves in the oil line.

Such apparatus is complex and expensive.

Another apparatus by U.S. Pat. No. 4,892,112 also provides the cleaning and/or lubricating of the medical/dental tool, i.e. the care of dental instruments which is connectable at its inlet to a pressurized gas source and at its outlet to the inlet sleeve of the dental instrument to be serviced, which hand tool is provided with at least one container for receiving the agent and connected to the pressurized gas line leading form the inlet to the outlet of the hand tool. The apparatus permits a troublefree metering in of even highly viscous agents for the care of the instrument and the dispensing of various amounts of the agents. This is achieved by providing a pressure control valve from which a pressurized gas line leads to the outlet of the hand tool downstream of the inlet of the hand tool and by providing at least one pump for conveying the agent, the intake line of the pump being connected with the at least one container for receiving the agent and the pressure line being connected with the pressurized gas line leading to the outlet of the hand tool in a site downstream of the pressure control valve and upstream of the outlet of the hand tool. The apparatus includes a pressurized gas source, preferably the dental unit provided in each dental practice, is connected at the inlet of the hand tool. The tool is plugged onto the turbine tube in place of the turbine angle piece by means of the provided quick-turn coupling, if no such coupling is provided, it is screwed onto the thread of the tube. On actuating the foot pedal of the dental unit, namely on turning on the turbine angle piece not present now, air is introduced into the hand tool with the flow pressure adjusted for the turbine of normally about bar. A pressure control (safety) valve reduces this pressure to about bar without subjecting the tubes of the dental unit to stress. The compressed air is now further conveyed through the pressurized gas line to the outlet where turbine angle pieces and tool holders and angle pieces of the most diverse kinds (not represented), termed dental instruments for short in the following, can be plugged on by means of exchangeable and sealing adapters, for instance the elastic connecting sleeves. The apparatus also comprises two storage containers for cleaning (disinfecting) and lubricating agents from which these cleaning and lubricating agents, called agents for short in the following, are sucked via intake lines by means of two manually actuated reciprocating pumps and can be injected under pressure independently of one another into the pressurized gas line, so that the pressurized gas charges the agents into the dental instrument plugged on. For this purpose, the pressure line emanates from each pump and terminates together with the pressurized gas line in a metering or mixing chamber disposed in flowing direction upstream of the outlet, etc.

This apparatus requires the pump presence and has the same deficiency as the above described apparatus, i.e. such apparatus is complex and expensive.

Another U.S. Pat. No. 5,505,218 provides the cleaning of the dental tool in a washing container filled with liquid, particularly water, using the ultrasonic effect. The device comprises a pot-shaped washing container with a multiplicity of mountings in the interior of the container each for one tool holder/handpiece (tooth drill), a water supply system, with which water can be supplied to the washing container and can also be lead from it, a compressed air supply system, a care agent supply system and an ultrasonic cleaning device, of which only one ultrasonic transducer for applying ultrasound to the washing container is illustrated. The washing container has a supply and discharge line, which is part of the water supply system, and with a water outlet. The following are arranged downstream of each other in the direction of flow, in the water supply line which is connected to a water connection: a first solenoid valve, a pump, a softening device and a condenser. The softening device is connected directly to the water outlet by means of a discharge line in which two solenoid valves are arranged one behind the other, so that the waste water can be directly discharged into the water outlet. Also, device includes the compressed air supply system having five compressed air lines connected in parallel, an electrically powered air heater, etc.

Such apparatus does not provide the cleaning of the dental burrs and brushes and is used for the handpiece and mostly drills cleaning.

Thus, there is a great need in the art for the improved dental (medical) tool cleaning apparatus, providing convenient, economical and effective cleaning of the dental tool (e.g. burrs and files/brushes) exposed to one patient's mouth of the remained tooth material on the tool between operations on patients, thereby providing a safeguard against the spread of disease.

OBJECT AND ADVANTAGES OF THE INVENTION

Accordingly, several objects and advantages of the present invention are to provide convenient, economical and effective cleaning of the dental/medical tool.

It is another object of the invention to eliminate necessity of the hand-labor process of the dental/medical tool cleaning.

It is still another object of the invention to reduce the time of the dental/medical tool cleaning.

It is further object of the invention to increase the a safeguard against the spread of disease.

Still, further objects and advantages will become apparent from a consideration of the ensuing description accompanying drawings.

DESCRIPTION OF THE DRAWING

In order that the invention and the manner in which it is to be performed may be more clearly understood, embodiments thereof will be described by way of example with reference to the attached drawings, of which.

SUMMARY OF THE INVENTION

A cleaning apparatus for medical and/or dental tool provides a possibility to clean the burrs and brushes (files) of the remained tooth material on them after operation on patient. An improved cleaning apparatus for medical and/or dental tool includes a container, comprising a neck with an opening and at least one of a plurality of apertures located in the lower part of the neck, a fluid stream reflector of a lid, which includes a connector comprising inlet pipe, which is coupled by a tubular means with a fluid line via controllable valve, and a cylindrical stand connected to the base providing stable position of the container during cleaning process.

DESCRIPTION OF THE PREFERRED EMBODIMENTS

Here the description of an improved cleaning apparatus for medical and/or dental tool will be done in statics (as if the components of the improved apparatus are suspended in the space) with description of their relative connections to each other. The description of the functional operations of an improved apparatus will be done hereinafter.

Figure 1:
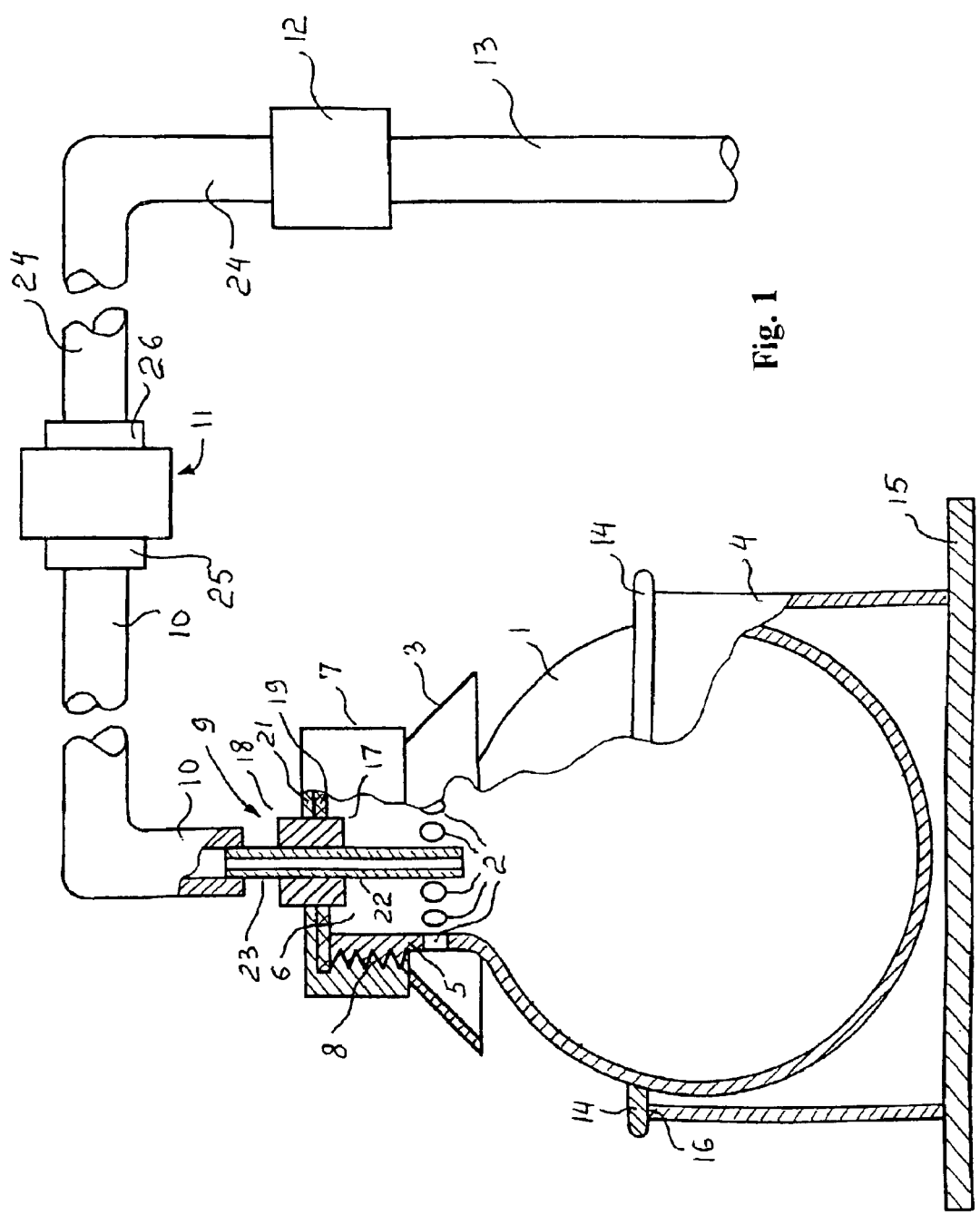
FIG. 1 is a simplified drawing of an improved cleaning apparatus for medical and/or dental tool.
Figure 3:
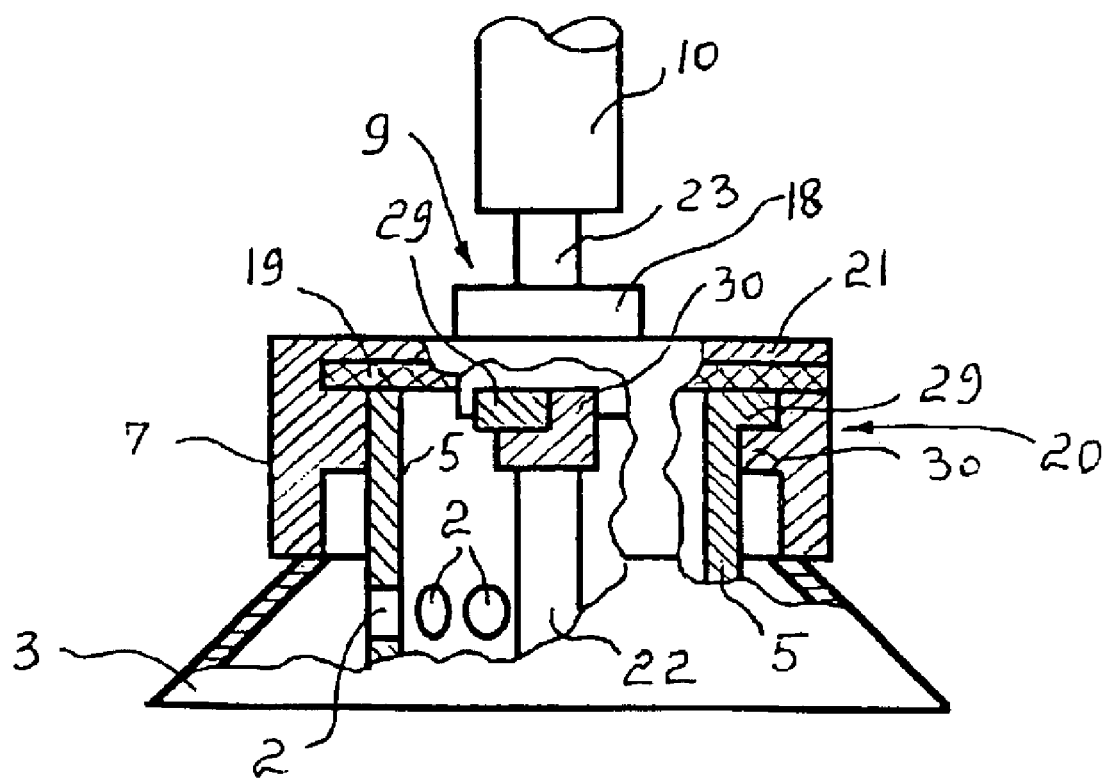
FIG. 3 is a simplified drawing of the second variant of the container and lid coupling.

An improved cleaning apparatus for medical and/or dental tool includes a container 1, preferebly of spherical form, as shown on FIG. 1. The container 1 can also be of two hemispherical bodies connected to each other or any geometrical form/configuration providing turbulent movement of the cleaning agent (fluid/liquid—preferably water) inside of container 1. The container 1 includes support 14 rested on the rims 16 of the hollow cylindrical stand 4 connected to the base 15. Also, the container 1 includes an upper portion (neck) 5 significantly smaller in diameter from the lower portion of the container, as shown on FIGS. 1, 3. The neck 5 can have, for example, an outer thread 8 to be coupled with the lid 7, having an inner thread, as shown on FIG. 1, or can be coupled with the lid 7 by a clipping lock 20 shown on FIG. 3. The clipping lock 20 includes at least two of a plurality of corbels 29 extended from the outer side of neck 5, and the adequate quantity of hooks 30 extended from the inner side of the lid 7. The gasket 19, inserted in the lid 7, provides tight non-leaking coupling of the container 1 and lid 7. The connector 9, comprising a fluid inlet portion 18 and fluid outlet portion 17, is installed into the top 21 of the lid 7 in such manner, that the fluid inlet portion 18 of the connector 9 is located over outer side of top 21 of the lid 7, and the fluid outlet portion 17 of the connector 9 is located under inner side of top 21 of the lid 7 in the opening 6 of the neck 5. The connector 9, for example, can be sealed to the top 21 in order to provide non-leaking connection, and for example can be presented by piece of pipe/tube. The fluid inlet portion 18 includes an inlet pipe 23 to be connected to the one side of the outlet tubular means 10, another side of which is connected to the output 25 of the controllable valve 11. The input 26 of the controllable valve 11 is connected to the one side of the inlet tubular means 24, another side of which is via fluid line valve 12 is connected to the fluid line 13. The fluid outlet portion comprises an outlet pipe 22.

The fluid stream reflector 3 is a ring of the truncated conic configuration. The fluid stream reflector 3 is rigidly connected (non-leaking connection) to the lid 7 (the lid 7 can have solid body with the lower part adequate to the fluid stream reflector 3). The fluid stream reflector 3 is intended for reflection of the exhausted agent (liquid/water) in the direction down. The neck 5 includes the apertures 2 located in the lower part of the neck 5. The longitudinal (horizontal) axes of the apertures 2 is preferably coincident with the upper half-portion of the fluid stream reflector 3. The ratio of diameter "D" of the container 1 to diameter "$d_1$" of the apertures 2 and the ratio of diameter "D" of the container 1 to inside diameter "$d_2$" Of the fluid outlet portion 17 can approximately be $D/d_1=30/1$ and $D/d_2=20/1$ respectively to provide the efficient turbulence of the cleaning fluid inside container 1. The ratios $D/d_1$ and $D/d_2$ is not limited by given numbers, and can be selected in compliance with the other characteristics, e.g. according to the following approximate equation: $T=f(V_F, R_1, R_2, N, L)$, wherein T—turbulence, $f$—function, $V_F$—fluid flow speed, $R_1$—ratio D to $d_1$, $R_2$—ratio D to $d_2$, N—quantity of the apertures 2, and L—length of the outlet pipe 22 of the connector 9.

Figure 2:
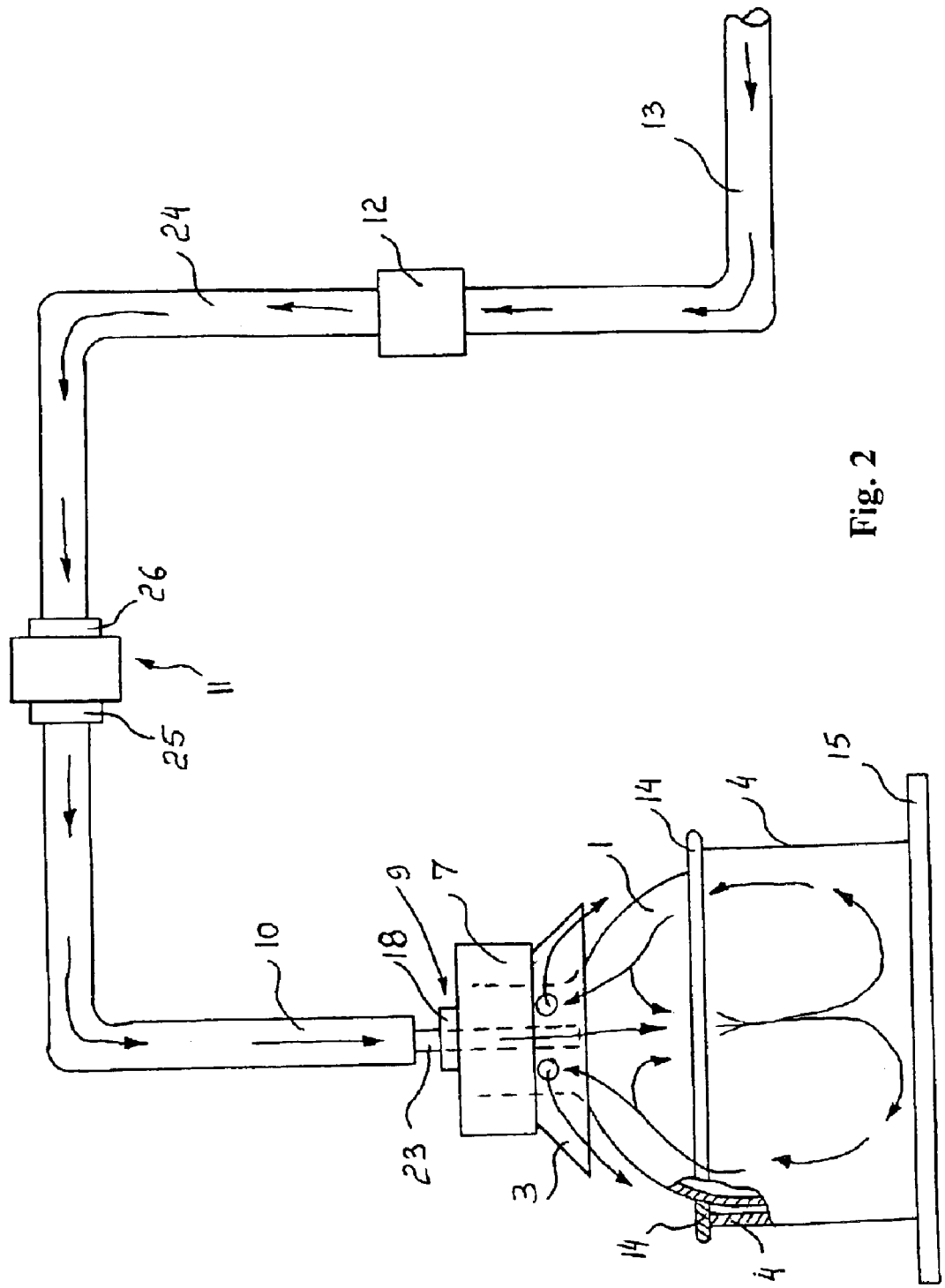
FIG. 2 is a simplified illustration of the cleaning fluid flow.
Figure 4:
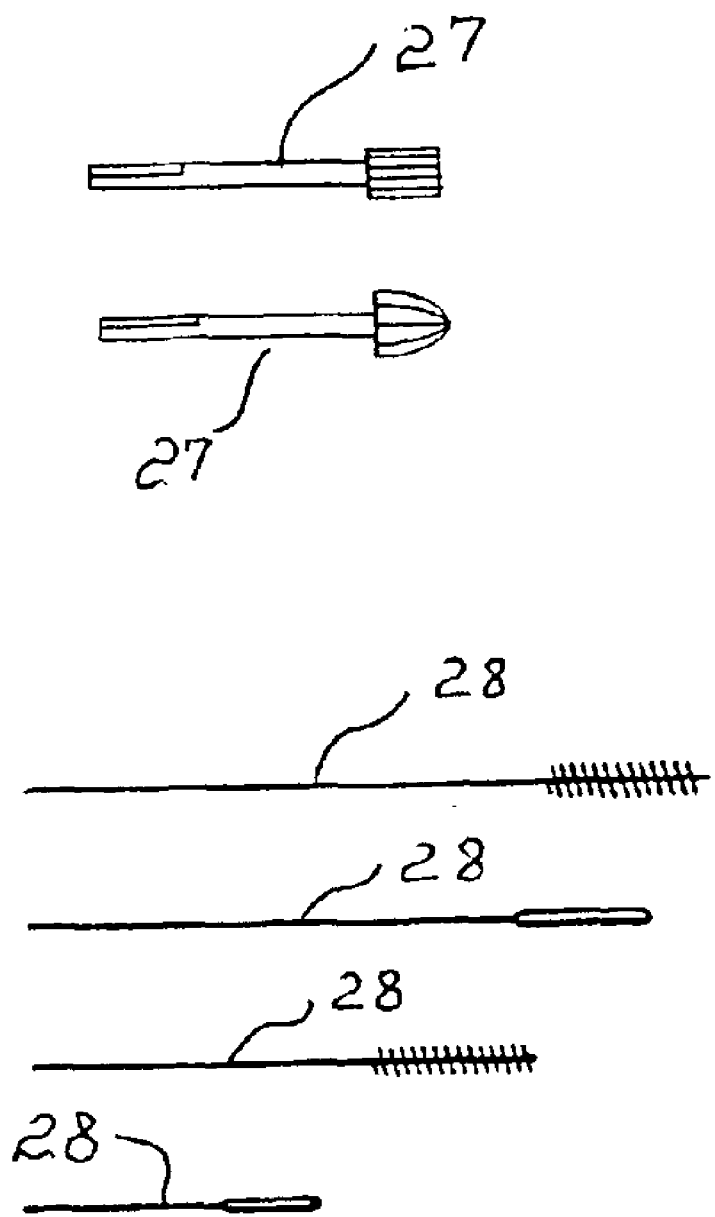
FIG. 4 is a simplified illustration of the dental tool.

The improved cleaning apparatus for medical and/or dental tool operates as follows below. The burrs 27 and files (brushes) 28, shown on FIG. 4, are placed inside container 1. The lid 7, including fluid stream reflector 3, is assembled with the gasket 19 and connector 9 and coupled with the neck 5 of the container 1. The container 1 is installed in the cylindrical stand 4 and rested by its support 14 on the rim 16 of the cylindrical stand 4 connected to the base 15 in order to provide the stable position of the container 1 during cleaning process. The outlet tubular means 10 is connected to the inlet pipe 23 of the fluid inlet portion 18 of the connector 9, and to the output 25 of the controllable valve 11. The inlet tubular means 24 is connected to the input 26 of the controllable valve 11 and via fluid line valve 12 to the fluid line 13 (for example, to the water manifold/water line). The fluid line valve 13 is open and by opening of the controllable valve 11 is provided the fluid flow through connector 9 into container 1. The flow speed, sufficient to create a turbulent movements of the fluid and dental tool (burrs 27 and brushes 28) inside container 1, is regulated by the controllable valve 11. The cleaning agent flow direction is shown on FIG. 2. The excess of the agent is exhausted (outstreamed, drained) from the container 1 through the apertures 2. As has been mentioned above, the outstream of the excess fluid is reflected by the fluid stream reflector 3 in the direction down. The fluid stream reflector 3 can be of any configuration (for instance, a form of spherical segment /not shown/, etc.), providing the prevention of sprinkle of the excess agent all over around in the horizontal direction through the apertures 2. The cleaning cycle is depend on the characteristics of the improved cleaning apparatus for medical and/or dental tool, for example, such as $R_1=D/d_1$, $R_2=D/d_2$, N, etc. For instance, in practice for D=60 mm, $d_1$=2 mm, $d_2$=3 mm and N=12, the cleaning process of about 50–75 pieces of dental burrs takes about 5 minutes.

Thus, an improved cleaning apparatus for medical and/or dental tool provides convenient, economical and effective cleaning of the dental tool (e.g. burrs and files/brushes) exposed to one patient's mouth of the remained tooth material on the tool between operations on patients.

CONCLUSION, RAMIFICATION AND SCOPE

Accordingly the reader will see that, according to the invention, I have provided a cleaning apparatus for medical and/or dental tool, providing convenient, economical and effective cleaning of the dental tool (e.g. burrs and brushes) exposed to one patient's mouth of the remained tooth material on the tool between operations on patients. An improved cleaning apparatus for medical and/or dental tool has various possibilities, considering activities of the cleaning devices.

While the above description contains many specificities, these should be not construed as limitations on the scope of the invention, but as exemplification of the presently-preferred embodiments thereof. Many other ramifications are possible within the teaching to the invention. For example, an improved cleaning apparatus for medical and/or dental tool eliminates the necessity of the dentist's staff hand-labor activity, providing more time for them to use for patients. Also an improved cleaning apparatus for medical and/or dental tool can be used for disinfecting agent too, thereby providing a higher degree of safeguard.

Thus, the scope of the invention should be determined by the appended claims and their legal equivalents, and not by examples given.

THE DRAWING REFERENCE NUMERALS WORKSHEET

1.—a container;
2.—an aperture;
3.—a fluid stream reflector;
4.—a cylindrical stand;
5.—a neck;
6.—an opening;
7.—a lid;
8.—a thread;
9.—a connector;
10.—an outlet tubular means;
11.—a controllable valve;
12.—a fluid line valve;
13.—a fluid line;
14.—a support;
15.—a base;
16.—a rim;
17.—a fluid outlet portion;
18.—a fluid inlet portion;
19.—a gasket;
20.—a clipping lock;
21.—a top;
22.—an outlet pipe;
23.—an inlet pipe;
24.—an inlet tubular means;
25.—an output;
26.—an input;
27.—a burr;
28.—a file (brush);
29.—a corbel;
30.—a hook.

What is claimed is:

1. A cleaning apparatus for medical and/or dental tool comprising
   a container including an upper portion with an opening and at least one of a plurality of apertures located in the lower part of said upper portion, and wherein said container, including said medical and/or dental tool, is rested by a support on a rim of a cylindrical stand connected to a base of said cleaning apparatus for said medical and/or dental tool;
   a lid including a fluid stream reflector located in the lower part of said lid and a connector installed in a top of said lid, and wherein said connector comprises a fluid outlet portion including an outlet pipe located in said opening of said upper portion of said container, and a fluid inlet portion comprising an inlet pipe;
   a controllable valve connected by an outlet tubular means to said inlet pipe of said fluid inlet portion of said connector and by an inlet tubular means through a fluid line valve to a fluid line.

2. The apparatus of claim 1, wherein said connector is rigidly connected to said lid providing non-leaking their connection.

3. The apparatus of claim 1, wherein said lid further includes a gasket providing non-leaking coupling of said lid with said container.

4. The apparatus of claim 1, wherein said upper portion of said container and said lid are coupled by a threaded connection, and wherein said threaded connection is provided by the thread on an inner side of said lid and on an outer side of said upper portion of said container.

5. The apparatus of claim 1, wherein further said lid and said upper portion of said container are coupled by a clipping lock comprising at least two of a plurality of corbels extended from said outer side of said upper portion of said container, and an adequate quantity of hooks extended from said inner side of said lid.

* * * * *